(12) United States Patent
Sarver et al.

(10) Patent No.: US 6,234,631 B1
(45) Date of Patent: May 22, 2001

(54) COMBINATION ADVANCED CORNEAL TOPOGRAPHY/WAVE FRONT ABERRATION MEASUREMENT

(75) Inventors: Edwin J. Sarver, Merritt Island, FL (US); David Liu, Irvine, CA (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

(21) Appl. No.: 09/521,855

(22) Filed: Mar. 9, 2000

(51) Int. Cl.[7] ............................................. A61B 3/10
(52) U.S. Cl. ............................................. 351/212
(58) Field of Search ............................ 351/205, 206, 351/211, 212, 246; 606/4, 5

(56) References Cited

U.S. PATENT DOCUMENTS

| | | |
|---|---|---|
| 5,227,818 | 7/1993 | El Hage . |
| 5,777,719 * | 7/1998 | Williams et al. ..................... 351/212 |
| 6,007,204 * | 12/1999 | Fahrenkrug et al. ................. 351/205 |

* cited by examiner

Primary Examiner—George Manuel
(74) Attorney, Agent, or Firm—William H. Bollman

(57) ABSTRACT

A method for the simultaneous measurement of the anterior and posterior corneal surfaces, corneal thickness, and optical aberrations of the eye. The method employs direct measurements and ray tracing to provide a wide range of measurements for use by the ophthalmic community.

4 Claims, 19 Drawing Sheets

Block diagram of combination advanced corneal topography/wave front aberration measurement system.

Block diagram of combination advanced corneal topography/wave front aberration measurement system.

Sequence of events for exam

FIG. 3    Pupil Contour

Ray tracing a light segment from a source through the cornea and back to a camera.

Horizontal and vertical cross sections projected onto eye.

Corneal front surface measurement coverage
using three cameras.

Corneal front surface

Corneal thickness measurement using ray tracing of pupil contour

Ray tracing to compute corneal back surface and thickness

Wave front aberration

Estimation of
fovial spot locations

Offset determination

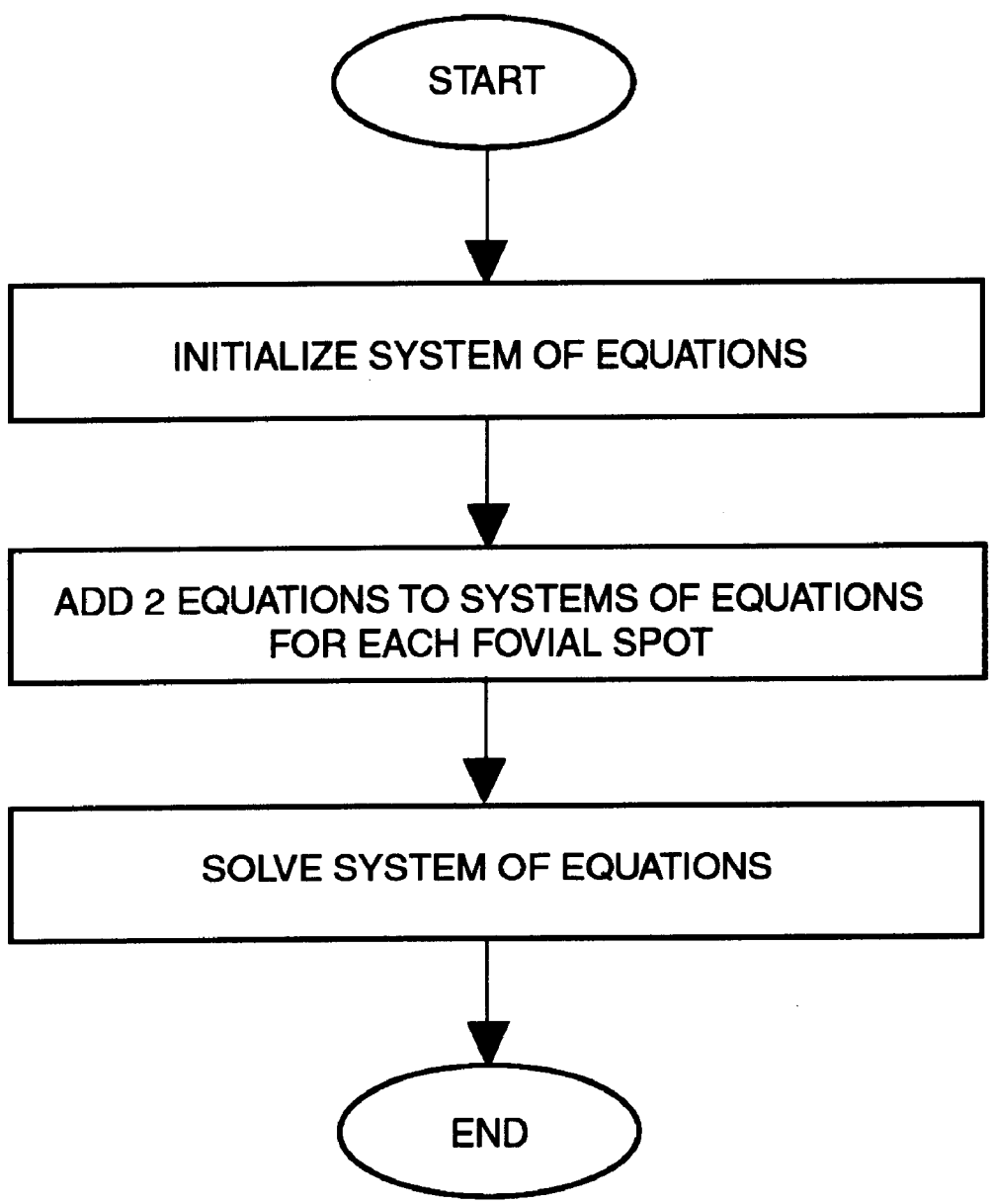
FIG. 11C    Fitting surface to the wavefront

Typical corneal topography system.

Corneal topography system with small keratoscope target to try to measure peripheral cornea.

Projecting a cross pattern on the cornea.

Basic idea of Hartmann-Shack wave front aberration measurement.

Effect of aberrated wave front on lenslett array/CCD image.

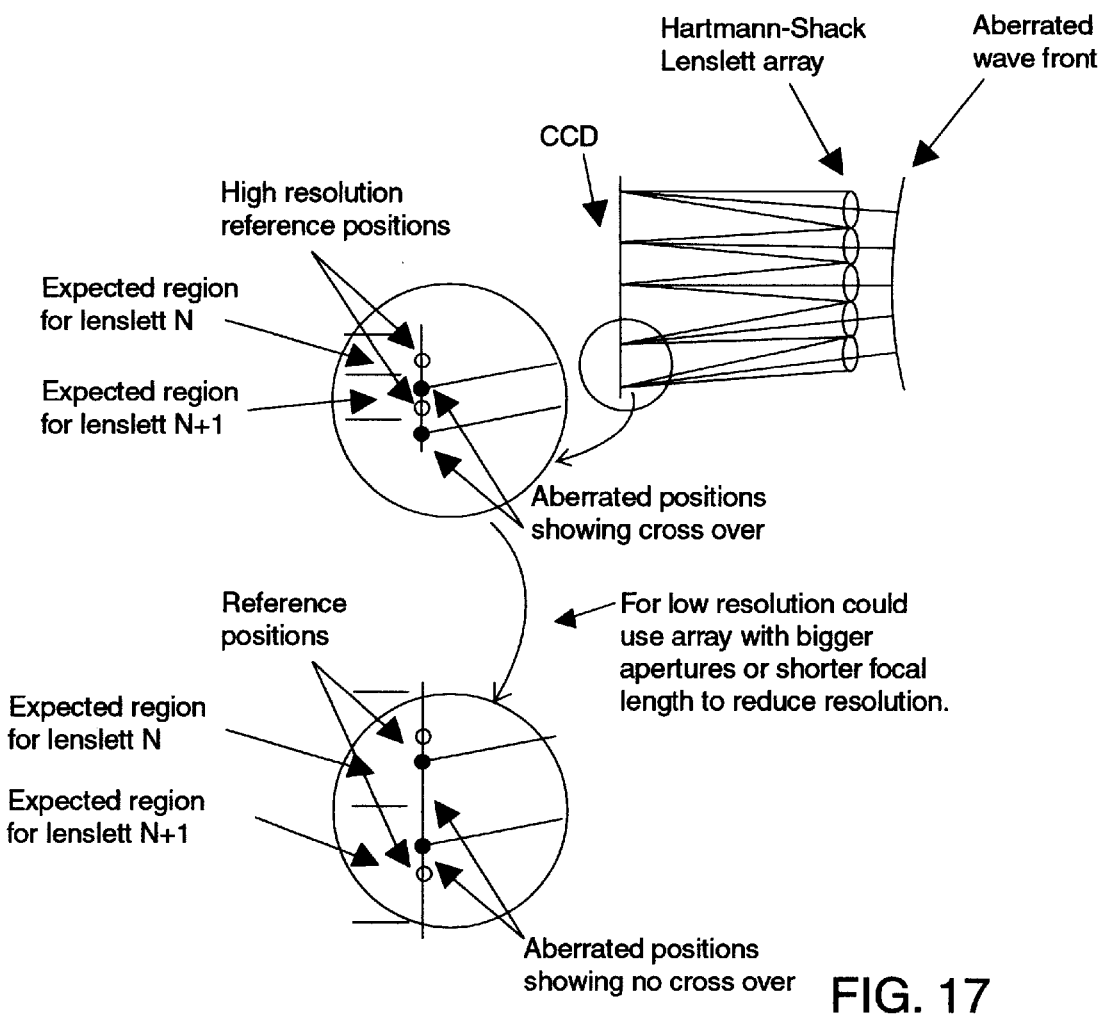
Use of multi-resolution micro-lens arrays to solve problem of point cross-over.

COMBINATION ADVANCED CORNEAL TOPOGRAPHY/WAVE FRONT ABERRATION MEASUREMENT

BACKGROUND OF THE INVENTION

1. Field of the Invention

This invention relates generally to apparatus for use in determining the front and back contours of the cornea of a human eye and thus facilitating the diagnosis and evaluation of corneal anomalies, design and fitting of contact lens, and the performance of surgical procedures. The present invention also relates to the field of measurement of the refractive characteristics of an optical system, and more particularly, to automatic measurement of the refractive characteristics of the human or other animal eye and to corrections to the vision thereof.

2. Background of Related Art

Corneal Front Surface Measurements

The cornea, being the front surface of the eye, provides the majority of the refracting power (about $2/3$) of the eye and is important to quality of vision. Recently, a number of corneal surgical techniques have been developed for correcting visual deficiencies, such as near-sightedness, far-sightedness and astigmatism. In order to assist with such surgical techniques, a number of devices have been proposed or developed to evaluate the topography, i.e., the shape or curvature, of the cornea. In addition, such corneal topography techniques are useful for fitting contact lenses and for the diagnosis and management of corneal pathologic conditions, such as keratoconus and other ectasias. For example, prior to performing a corneal surgical technique to correct a refractive error, the patient is preferably screened using a corneal topography device to rule out the possibility of subclinical keratoconus.

Corneal topography is typically measured using a series of concentric lighted rings, known as a keratoscope pattern, shown in FIG. 12. In a typical embodiment, the keratoscope pattern (reflected image of rings on CCD) is created by a keratoscope target, consisting of illuminated concentric rings which emit light rays which are projected onto the cornea of the patient's eye. Light rays are reflected off the patient's cornea, and a portion of the light is captured by a camera lens and focused onto a CCD. A computer is utilized to analyze the captured image to identify any distortions in the captured image and thus calculate any deformations in the patient's cornea.

While conventional corneal topography devices have achieved significant success, such devices suffer from a number of limitations, which, if overcome, could significantly enhance their accuracy and utility. For example, commercially available topography devices, such as the design illustrated in FIG. 12, typically measure the topography of only a portion of the cornea. In the design shown in FIG. 12, the light beam is emitted from a large, backlit keratoscope target and is then reflected off the cornea. Thereafter, a portion of the light reflects off the cornea and is focused by the camera lens at the center of the keratoscope target onto the CCD. Using this same technique to attempt to image the peripheral portion of the cornea would require a very large extended keratoscope target as shown in the "imaginary extension" of FIG. 12. This imaginary extension could not be realized in a real system due to size and interference with the subject's head. Therefore, such prior art devices are unable to measure the peripheral cornea.

To overcome this problem, other corneal topography devices have attempted to capture the light rays reflected from the peripheral portions of the cornea by designing a very small keratoscope target in the shape of a cylinder or cone, as shown in FIG. 13, encompassing the peripheral cornea. In this manner, light rays emitted by the cylindrical or conical keratoscope target will form a pattern of illuminated rings which will be reflected off the cornea. The reflected light rays, including light rays reflected off the peripheral portions of the cornea, will be captured by the lens and imaged onto the CCD. For this strategy, however, the cylindrical or conical keratoscope target must be positioned very close to the eye, and thereby tends to impinge on the patient's brow and nose. In addition to being potentially uncomfortable and potentially contributing to the spread of disease, the close approach of the keratoscope target makes the design very error-prone, as a slight error in alignment or focusing causes a large percentage change in the position of the keratoscope rings relative to the eye and, hence, a large error in the measurement of the cornea.

In addition, current systems tend to provide poor pupil detection and do not accurately measure non-rotationally symmetric corneas, such as those with astigmatism. The location of the pupil is particularly important in planning surgical procedures for correcting visual deficiencies. In current systems, pupils are typically detected by deciphering the border of the pupil from the image of the keratoscope rings. This is particularly difficult with conventional designs, however, as the intensity transition from the black pupil to a dark iris is minimal compared to the intensity transition from a bright keratoscope ring image to a dark interring spacing. As a result, the pupil detection algorithms in current systems often fail or provide poor results.

In a recent corneal topography advancement, Malone (U.S. Pat. No. 5,873,832) describes a technique which utilizes a virtual image of a keratoscope pattern. The topography system reflects a structured light pattern off the cornea where light rays travel perpendicular to the cornea. In this manner, more of the peripheral cornea is imaged. The geometry of these reflected rays is similar to that of the innermost rays of the traditional corneal topography system. It is well known that the innermost data of traditional corneal topography systems have relatively low accuracy, so it is likely that this new technique will have lower accuracy than that currently provided by the commercially available corneal topography systems.

In the present invention, we overcome these problems of cornea measurement coverage and accuracy using a novel skew-view corneal analysis technique as explained below. We make use of three cameras as was detailed by Sarver (U.S. Pat. No. 5,847,804). While Sarver specifically used a front-view camera and two orthogonal side view cameras (only one of which was used during an exam), the present invention uses a front-view camera and a left- and right-camera oriented at 45 degrees to the optical axis of the front-view camera and all three cameras are used for each exam.

Cornea Back Surface Measurements and Cornea Thickness

Corneal thickness is commonly measured using an ultrasound technique. The hand held A-scan ultrasound probe produces a single-point measurement of the thickness of the cornea. This single point is, in reality, the average thickness of an area of several square millimeters in extent. Because the location of the measurement is dependent upon the operator's positioning, the location of the measurement is not exactly repeatable, hence the data is variable as well.

Another method is the scanning slit technique reported in Snook (U.S. Pat. No. 5,512,966), Knopp (U.S. Pat. No. 5,870,167), and Lempert (U.S. Pat. No. 5,404,884). In these techniques a slit of light is passed through the cornea and the interface of the slit with the front and back surfaces is evaluated from a digitized image. Using this information and an estimate of the index of refraction of the cornea, the thickness of the cornea can be estimated. By scanning the slit over several portions of the cornea, the thickness of a significant portion of the cornea can be obtained. Since the diffuse interaction of the light slit and the cornea can be ill-defined, the image processing will not be exact and so the measurements will contain some amount of error. These techniques also suffer from the characteristic that a large number of images must be obtained and processed to estimate a large portion of the cornea. The result is a large amount of data to process and store as well as the complexity of registration of the images due to movement of the eye during the acquisition period. Even though advanced data compression techniques exist such as that developed by Sarver (U.S. Pat. No. 5,418,714), the images still must be decompressed prior to processing.

In the present invention we take a completely novel approach which eliminates these shortcomings. Using the same three cameras as used in the cornea front surface calculation, we image the pupil contour. A light pattern in the shape of a cross, similar to two simultaneously projected orthogonal slits, is projected onto the cornea. As illustrated in FIG. 14, this pattern is viewed by the front-view camera (C3) to image the horizontal portion of the cross and the left- and right-view cameras (C1 and C2) to image the vertical portion of the cross. This provides a starting point for the corneal thickness and corneal back surface measurements. Then, knowing the front surface, and the starting point provided by the horizontal and vertical thickness data, we find the back surface such that corresponding rays from the three camera views would trace through the cornea and intersect at the pupil contour. Details of this new process are presented below.

Wave Front Aberration Measurement of the Eye

In contrast with man-made optical systems, human and animal eyes are optical systems in which the individual internal components of a given eye are not normally separately accessible for either direct measurement or adjustment, the output of the optical system is not directly accessible for analysis and the characteristics of individual components change over time with growth, aging and other factors.

The most common reason for measuring the optical characteristics of a human eye is to determine a prescription for corrective lenses to correct vision problems. Such measurements of the optical characteristics of the eye have long been made by the actual or apparent substitution of lenses with various correction factors with the patient indicating the effect of each substitution in terms of the image being clearer or fuzzier. This technique determines an overall correction for the optical characteristics of the eye.

Such determinations are subject to experimental errors and such events as accommodation of the eye to the substituted lens in a manner which gives the impression that a particular correction is desirable, when in fact that correction is not optimum.

Further, these measurement techniques determine corrections which improve overall vision, but are limited in normal practice to prism, cylindrical and spherical corrections which are low order corrections to the patient's actual, detailed vision errors which include higher order terms or characteristics which these measurement techniques cannot determine.

For the most part these prior art measurement systems are subjective and require the active participation of the patient for their success. In such cases the ophthalmologist must rely on the patient to indicate accurately which images are clearer than others as an indication of the appropriate degree of correction. This requirement for active participation of the patient is a disadvantage in a number of circumstances such as in the diagnosis of small children who have difficulty in understanding what is being asked of them and prevents its use for infants who are incapable of indicating the effect of such lens substitutions.

The requirement for the active participation of the patient in the determination of the characteristics of the eye can have unfortunate effects. Some anomalous conditions result in permanent disabilities because they are not detected during infancy because of the inability of infants to communicate with ophthalmologists. For example, if one eye is in focus and the other is severely out of focus during the time the brain is developing its ability to interpret visual signals, then a permanent disability develops in which the out-of-focus eye is never able to contribute usefully to the brain's image recognition because of a lack of proper stimulation during the period in which the brain's image interpretation functions became established. A person suffering from this condition can tell with the affected eye whether the lines in an image are sharp or fuzzy, but cannot assimilate the perceived information into an image. Present subjective refraction measurement systems are incapable of determining the development of this condition in infants because they cannot accurately diagnose the visual acuity of the eye without the active participation of the patient.

A number of objective refractometers have been developed in the hope of overcoming these problems. However, each of these has had problems or deficiencies of its own. One common deficiency is accommodation by the eye being measured. Another common problem is determining and maintaining accurate alignment of the measurement system during the measurement cycle, since any misalignment can cause inaccurate results.

In recent years, substantial interest has developed in using laser sculpturing, i.e. ultraviolet (UV) light laser ablation, to shape the anterior surface of the cornea as a means of providing corrected vision in place of the use of glasses or contact lenses. U.S. Pat. No. 4,665,913, which is incorporated herein by reference, discloses a UV laser scanning ablation technique for shaping a cornea in which a laser beam which produces a small spot is scanned across the cornea to remove a desired thickness of corneal material on each scan. The area scanned is increased or decreased on subsequent passes to scan each portion of the corneal surface a number of times which is proportional to the thickness of material to be removed at that portion of the cornea.

An alternative to the direct shaping of the corneal surface, is to essentially permanently attach a lenticule to the cornea with the lenticule being shaped to provide the desired vision correction. We say "essentially permanent" because the intention is to leave the lenticule in place permanently, unless some problem should develop which requires its removal. Such lenticules themselves may be reshaped or re-profiled by laser ablation at the time of installation or subsequent thereto to compensate for changes in the overall characteristics of the eye. Such techniques are disclosed in more detail in U.S. Pat. No. 4,923,467, entitled, "Apparatus and Process for Application and Adjustable Re-profiling of Synthetic Lenticules for Vision Correction" by Keith P. Thompson, which is incorporated herein by reference.

In addition to the advantages provided by eliminating the need for eye glasses or contact lenses, both of these techniques are conceptually capable of providing substantial additional advantages in that each should, under proper control and with sufficiently detailed correction instructions, be able to produce fully asymmetric reshaping of the cornea in a practical manner, rather than being limited to the sphere, cylinder and wedge approximation mentioned previously. If the spatially resolved refraction data indicated by the scanning lasers is not available, the most effective plan may be to measure the preoperative spherical aberration of the corneal front surface and maintain this same aberration during the laser sculpting of the cornea (see Schwiegerling 1998). If the spatially resolved refraction data were available, the method of Klein (Klein 1998) could be used to plan the optimal scanning pattern to sculpt the cornea.

However, in order to provide such detailed correction, there is a need for measurement techniques which measure the shape of the cornea and the existing refraction characteristics of the eye with the same detail and precision as can be provided by the correction modality in order that the errors may be fully corrected in this manner.

A measurement system providing such a correction measurement should be fast and should measure the eye's detailed refraction characteristics referenced to the cornea as a function of position across the dilated pupil. This position-dependent measurement may be categorized as a spatially resolved refraction measurement because the refraction at each measurement region (point) is determined in that local measurement region independent of the refraction at other, non-overlapping measurement regions.

In Penney (U.S. Pat. No. 5,258,791) and He (He 1998) a flying spot spatially resolved objective autorefractometer is described which solves a number of these issues, but has inherent limitations of its own. For example, the design requires a sequence of measurements be made as a flying spot is scanned. The resulting system is complex and is subject to errors due to patient movement. A similar flying spot system could be constructed using the manual psychophysical system described in (Salmon 1998) which employs Smirnov's principal, which would have the same drawbacks as the Penney system.

Recently, Hartmann-Shack lenslett arrays (also known as micro-lens arrays) have been used to measure the entire wave front aberration of the eye (Salmon 1998, Liang 1997, Liang 1994). This method has much promise for solving the problems associated with the previous techniques. The basic idea for this method of wave front measurement is illustrated in FIG. 15. In FIG. 15 we illustrate an input laser source viewed by the eye such that it forms a diffuse point source at the fovia. This diffuse spot then acts as a point source as it exits the eye. As this wave front passes through the lenslett array, it is focused on the CCD. If the eye had perfect optics, the wave front exiting the eye would form a plane wave. In this case the fovial point source would appear on the CCD as a regular array of points of light and would match perfectly with the reference spot locations obtained during a calibration operation. In FIG. 16 we illustrate the effects of an aberrated wave front. Here the wave front is no longer a plane wave. As the wave front passes through each lenslett, the focused point on the CCD is deviated from the reference position according to the slope of the wave front at the lenslett. This deviation, dy, along with the focal length of the lenslett allows us to compute the local partial derivative of the wave front. The wave front is reconstructed by integrating all derivatives computed for each lenslett in the CCD image. Details of this reconstruction process are provided in the following paragraphs.

Implementations of these lenslett array systems have been limited to research laboratories for several reasons. First, the laser spot on the fovia must be in rather sharp focus on the CCD array to allow reliable measurements. In these laboratory systems, this is usually accomplished by imaging through the subject's spectacle correction. In a clinical setting where exam time is important, finding which spectacle correction to use for each subject may be time prohibitive. A more serious drawback is the problem of point "cross-over" shown in FIG. 17. This occurs when the wave front has so much aberration that the fovia point sources associated with a given lens is mistakenly assigned to a neighboring lenslett. When this happens, the sign and/or magnitude of the partial derivatives of the wave front will contain a huge error. Another issue is the choice of reference axis of the wave front aberration. It was demonstrated by Cui (Chi 1998) that different wave front aberrations result as various reference axes are chosen. Since clinicians will want to register the wave front aberration data with the corneal surface and thickness data, this issue must be resolved for the situation where one instrument is used for corneal measurements and another is used for aberration measurement.

In the present invention, we solve each of the current drawbacks to typical Hartmann-Shack lenslett array based aberration measurement. First, we provide a simple focus adjustment mechanism which can account for at least +/−10 diopters of focus error. We also provide both high-resolution and low-resolution wave front analysis paths, so we can easily and effectively solve the point "cross-over" problem and increase the total number of data points being processed per exam. The complex issue of registering the corneal surface measurements with the aberration measurement is automatically solved by integrating both systems and providing simultaneous measurements in a single exam.

In addition to these individual benefits over the existing state of the art in measuring the corneal front surface, corneal back surface and thickness, and wave front aberration, we integrate these usually separate ocular measurement functions into a single instrument. This provides the additional benefits of:

(1) A more economical system compared to the combined cost of individual instrument.

(2) Reduced exam time since several measurements are made simultaneously.

(3) Data and exams are integrated into the same computer and database.

SUMMARY OF THE INVENTION

A method for the simultaneous measurement of the anterior and posterior corneal surfaces, corneal thickness, and optical aberrations of the eye. The method employs direct measurements and ray tracing to provide a wide range of measurements for use by the ophthalmic community.

BRIEF DESCRIPTION OF THE DRAWINGS

Features and advantages of the present invention will become apparent to those skilled in the art from the following description with reference to the drawings, in which:

FIG. 11C is a process flow diagram showing an exemplary process of fitting a surface to a wave front determined as shown in FIG. 10.

FIG. 17 is a representation of multi-resolution micro-lens arrays to solve the problem of point cross-over.

DETAILED DESCRIPTION OF ILLUSTRATIVE EMBODIMENTS

The present invention improves upon prior art by (1) using the proven accuracy of the keratometric target in a novel way to obtain full limbus-to-limbus coverage on the corneal front surface; (2) obtaining surface measurements of the corneal back surface using both a new projected light and a new ray tracing approach; (3) obtaining corneal thickness information from the corneal surfaces; (4) obtaining wave front aberration information for the entire eye using a multiple resolution micro-lens array technique; and (5) obtaining all these measurements simultaneously.

One embodiment of the invention consists of the corneal measurement components, the wave front aberration components, the computer, and the software as described below.

Figure 1:
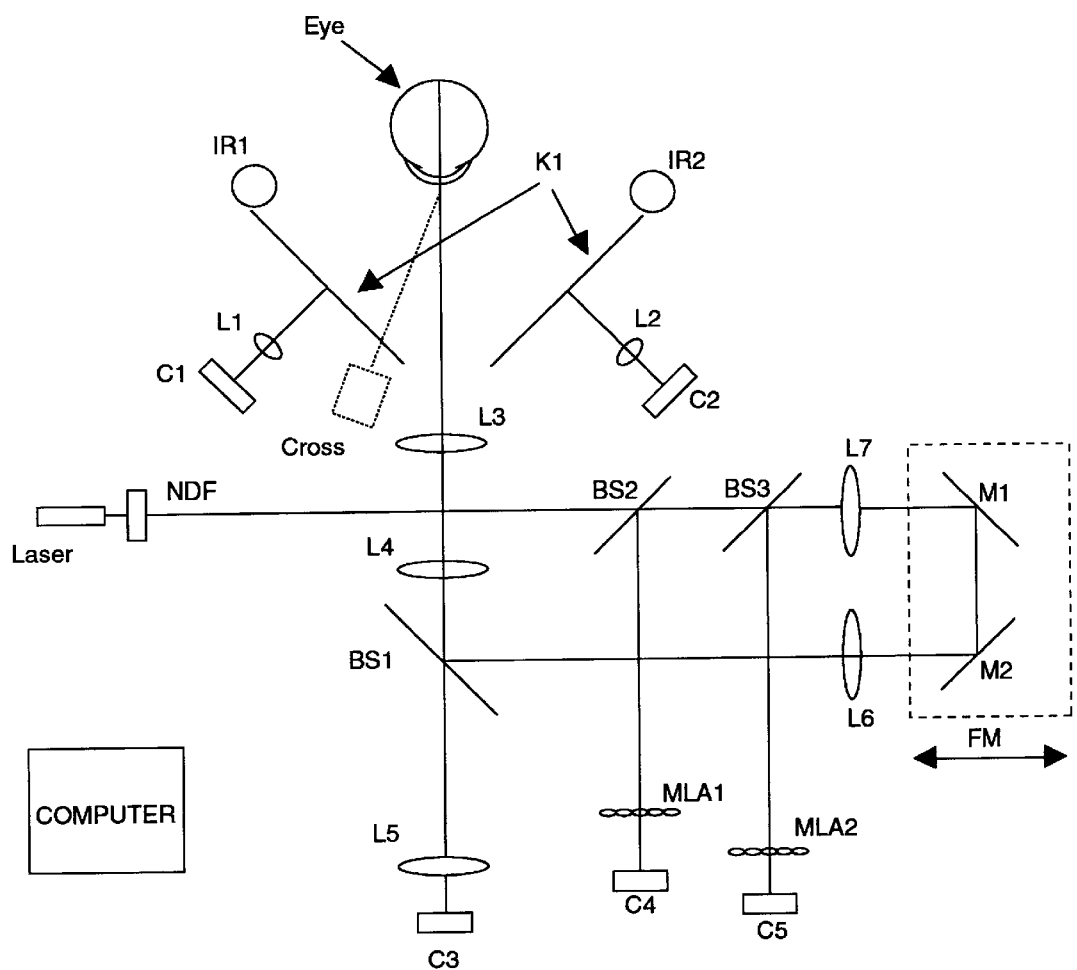
FIG. 1 is a representation of the layout of the combined advanced corneal topography/wave front aberration measurement system.

In FIG. 1 we show a block diagram of the major components of the advanced corneal topography/wave front aberration measurement (ACT/WAM) system. The system consists of a keratometric target source (K1) with illumination source (not shown), projected cross source (Cross), a diode laser (Laser), neutral density filter (NDF), multiple resolution micro-lens arrays (MLA1 and MLA2) with imaging cameras (C4 and C5), a front view camera (C3), front view camera lens (L5), left- and right-view cameras (C1 and C2) oriented at a skew angle with respect to the eye (Eye), left- and right-view camera lenses (L1 and L2), a focusing mechanism (FM), IR floodlamps (IR1 and IR2), relay lens system (L3 and L4), beam splitters (BS1, BS2, and BS3), focusing relay lens (L6 and L7), mirrors (M1 and M2), and a computer (Computer) with video digitizer card(s).

The light path for the aberration wave front measurement is as follows. The laser light is attenuated by a neutral density filter (NDF) so that the power entering the eye (Eye) is at a safe level according to ANSI Z136.1-1993. The laser then passes through the beam splitters (BS2 and BS3), the focusing mechanism (lenses L6 and L7 and mirrors M1 and M2), beam splitter (BS1), the relay lens (lenses L3 and L4), and finally enters the eye. In the eye, the laser is (approximately) focused on the fovia where it is diffusely scattered. The focusing mechanism is used to bring the laser into reasonably sharp focus. This diffuse laser spot then takes the role of a point source for the reverse (measurement) path. The light from the diffuse laser spot travels out of the eye, through the relay lens (L3 and L4), is reflected by beam splitter (BS1), goes through the focusing mechanism (lenses L6 and L7 and mirrors M1 and M2), and then is reflected by beam splitters BS1 and BS2 to the micro-lens arrays (MLA1 and MLA2). The lenses are selected so that the entrance pupil of the eye is conjugate to the micro-lens arrays and the diffuse spot on the fovia is conjugate with the micro-lens cameras (C4 and C5). As the micro-lens array focuses the diffuse spot onto the cameras, deflections from that generated by a perfect plane wave are determined and from these deflections, the aberration wave front is computed. For the total aberration, the required deflection from the focusing mechanism must be taken into account as described below.

The light path for the corneal measurements is as follows. The keratometric target source (K1) is reflected off the cornea and imaged by the left-, front-, and right-view cameras (C1, C2, and C3). The keratometric target source is turned off and the flood lamps (IR1 and IR2) and/or projected cross source (Cross) are turned on to allow the same three cameras to image the horizontal and vertical corneal surfaces, corneal thickness, and the pupil contour. These digitized images are processed as explained below.

Keratometric Target

Figure 6:
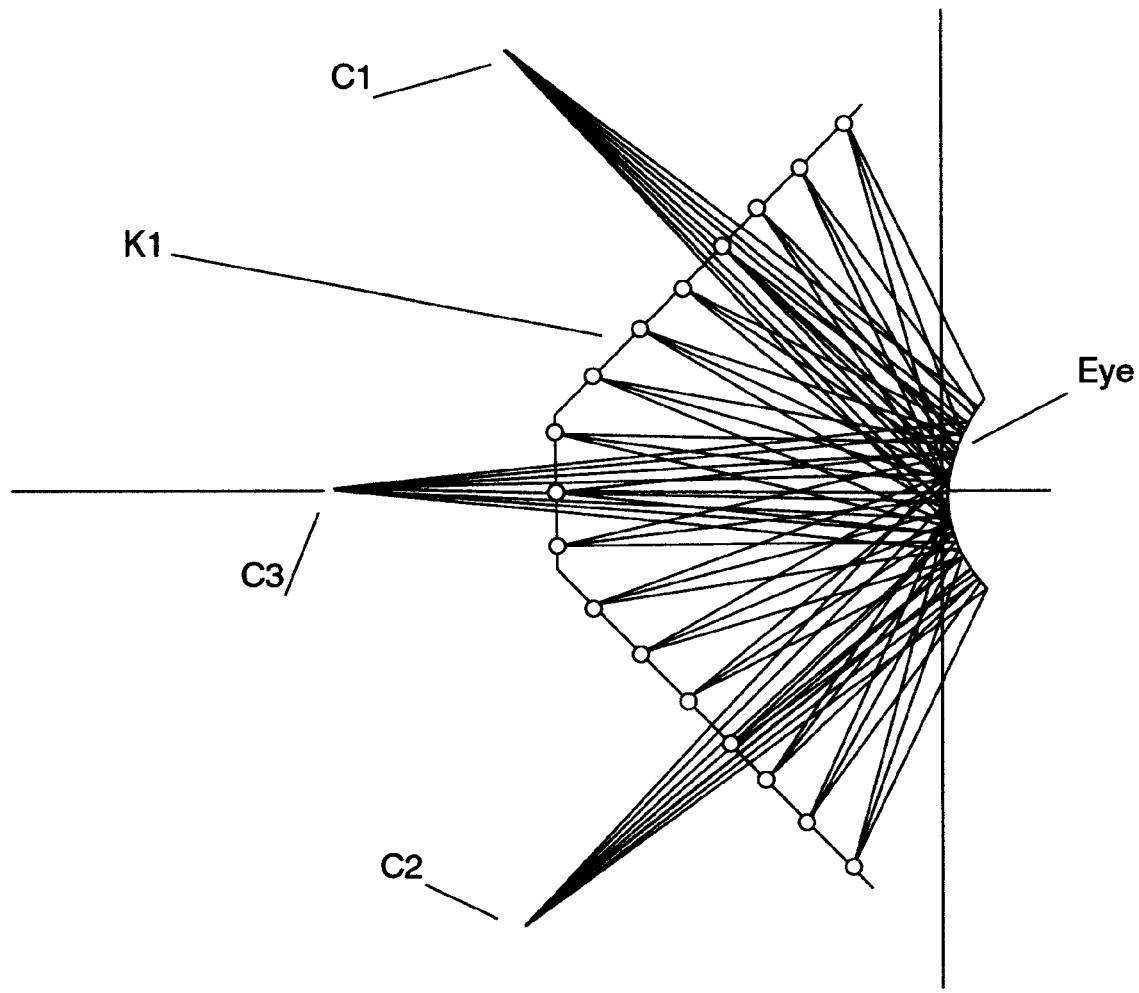
FIG. 6 is a representation of the corneal front surface measurement coverage for three cameras.

The keratometric target provides a pattern which is reflected off the cornea and imaged by the left-, front-, and right-view cameras (C1, C2, and C3). The pattern used in the keratometric target can be any pattern which is usually employed on corneal topography (Gills 1995). The preferred physical shape of the keratometric target is a cone. This shape has the advantage of yielding an image in good focus when reflected off the eye and can facilitate any desired target pattern just as claimed for the single-curvature placido plate in U.S. Pat. No. 5,864,383. An example of a suitable pattern is the polar checkerboard pattern of U.S. Pat. No. 5,841,511. Using the three camera views of the reflected keratometric target, we process the reflected image in an entirely different manner than that disclosed for the single view discussed in U.S. Pat. No. 5,841,511. The front view camera (C3) along with the keratometric target provides the function of the usual reflection-based corneal topography system (Gills 1995). The left- and right- view cameras (C1 and C2) provide the ability to measure the corneal front surface to the horizontal limbal margin. In FIG. 6 this feature is illustrated. Here the left-view camera measures the left corneal region, the front-view camera measures the central corneal region, and the right-view camera measures the right corneal region. Note that there is significant overlap between the regions. This overlap allows the generation of a mathematical representation of the front surface of the cornea as described in the algorithms below. The illumination source for the keratometric target is placed behind the translucent, conical body of the keratometric target to provide a uniform back light. It is composed of an array of IR LED's which can be turned on and off quickly during an exam.

Multiple Resolution Micro-Lens Arrays

As indicated above, one of the main problems with using micro-lens arrays to measure the wave front aberration is the possibility of spot "cross-over". This happens when there is so much aberration that the focused spot from one lenslett from the array crosses over into the region where the neighboring lenslett would normally image its focused spot. To solve this problem, a low resolution micro-lens array is used in addition to a high resolution micro-lens array. The low resolution array has a larger aperture and/or a shorter focal length compared to the high resolution array. In FIG. 17 we illustrate the cross over problem and show how it is solved with the use of the low resolution array. In the upper part of the figure, a highly aberrated wave front causes the lower two lenslets to be imaged outside their expected location regions. In this case the points would mistakenly be identified as belonging with the wrong lenslett and would in turn lead to an incorrect estimate of the partial derivatives of the wave front. In the lower portion of the figure we show the situation when we have a lower resolution array. In this case the aberrated position of the points falls within the expected location regions and the correct correspondence is made with the lensletts. There could be several strategies for using these multi-resolution arrays. Our approach is to use the low resolution array to estimate the aberrated wave front, then use this estimate along with optical ray tracing analysis to locate the expected position of the high resolution points. Details of this algorithm are presented below.

Sequence of Events for Exam

Figure 2:
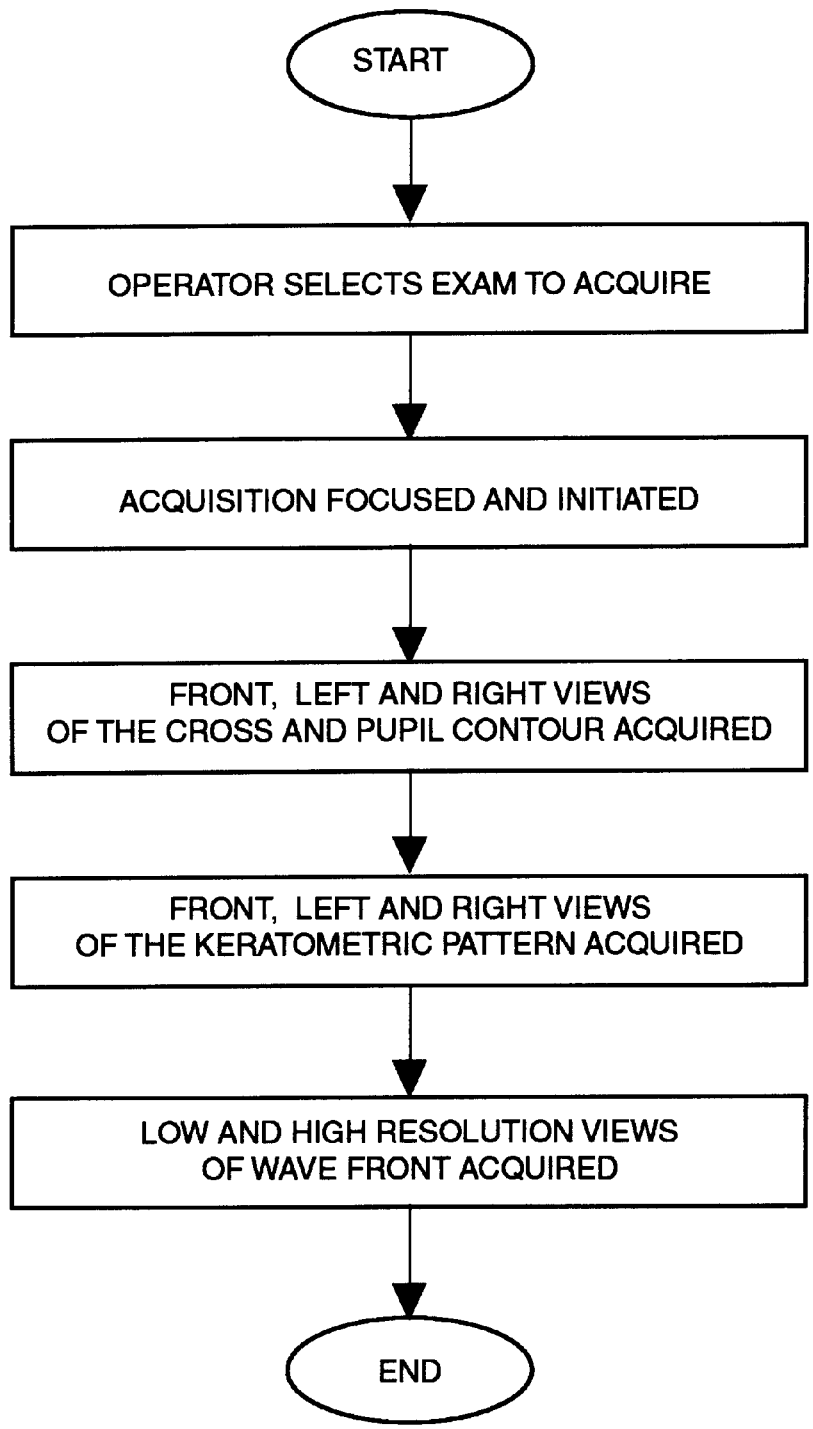
FIG. 2 is a process flow diagram showing an exemplary sequence of events, in accordance with the principles of the present invention.

FIG. 2 is a process flow diagram showing an exemplary sequence of events, in accordance with the principles of the present invention.

In particular, as shown in FIG. 2, the process of acquiring all of this data and performing the analysis prior to display and/or saving the data is performed in the following sequence of events:

1. Operator selects which exam data to acquire (cornea and/or wave front aberration).

2. Operator focuses and initiates an acquisition.

3. The front, left and right views of the cross and pupil contour are acquired.

4. The front, left and right views of the keratometric pattern are acquired.

5. The low and high resolution views of the wave front are acquired.

Key software components of the ACT/WAM system are: (1) pupil contour; (2) Horizontal and vertical sections of the cross projected onto the cornea; (3) Corneal front surface; (4) Corneal back surface; (5) Corneal thickness; and (6) Wave front aberrations of the eye.

Pupil Contour

Figure 3:
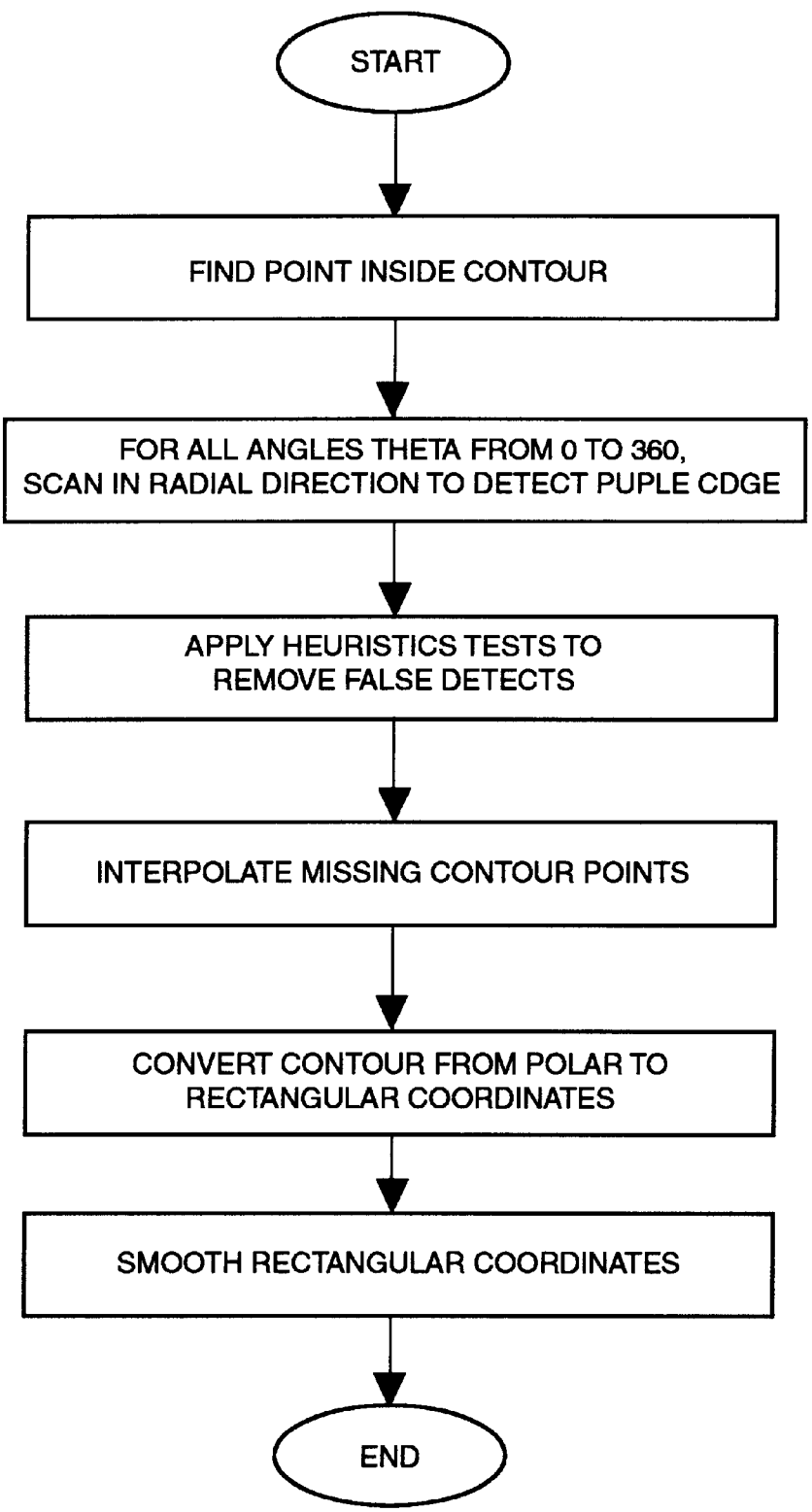
FIG. 3 is a process flow diagram showing an exemplary determination of a pupil contour, in accordance with the principles of the present invention.

FIG. 3 shows a process flow diagram showing an exemplary determination of a pupil contour, in accordance with the principles of the present invention.

In particular, as shown in FIG. 3, the processing of the pupil contour is performed on all three of the left-, front-, and right-view images. Since the illumination for this acquisition is near IR, all iris patterns appear to have about the same intensity so no special processing is required for light iris patients such as light blue, or for dark iris patients such as dark brown. The steps of the algorithm are:

1. Find point inside the contour.

2. For all angles, theta, from zero to 360 do the following:

3. Scan in a radial direction from the point found in step 1 in the direction of theta for a dark to light transition using a smoothed derivative operation. Store this point as a possible pupil contour point.

4. If not done scanning, continue with step 3 for next theta value.

5. Apply heuristics tests to remove false detects and move the contour as required.

6. Interpolate missing contour points.

7. Convert the contour from polar to rectangular coordinates.

8. Smooth the rectangular coordinates representing the pupil contour using a zero-phase low pass filter on the individual x and y coordinates.

Horizontal and Vertical Cross Sections Projected Onto the Eye

Figure 4:
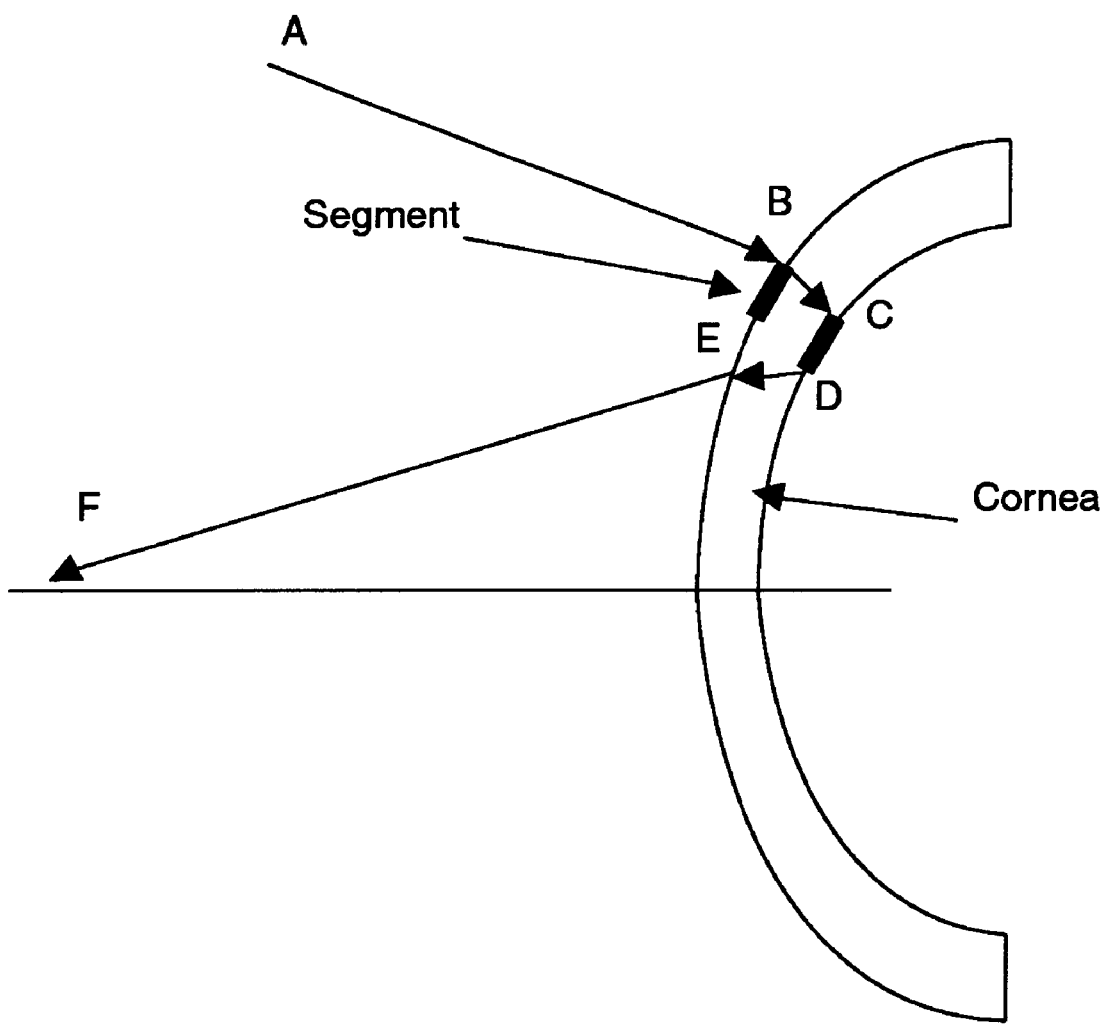
FIG. 4 is a representation of a ray tracing for a light segment from a source through the cornea and back to a camera.

The processing of the horizontal and vertical cross sections projected onto the eye is performed on all three of the left-, front-, and right-view images. The front-view image is processed for the horizontal section and both the left- and right-view images are processed for the vertical section. In FIG. 4 we show a ray tracing of a light segment from a source through the cornea and back to a camera. The source of the segment is at point A, a distal edge strikes the cornea at point B and the segment is refracted, a refracted proximal edge intersects the back corneal surface at D and part of the light is reflected to point E. At E the proximal edge is refracted to the camera point F. From calibration data we know the direction of the rays AB and EF. This together with an estimate of the index of refraction of the cornea and an estimate of the corneal front surface allow the ray tracing indicated in FIG. 4, and the solution of the corneal back surface point and thickness at the neighborhood of BCDE.

Figure 5:
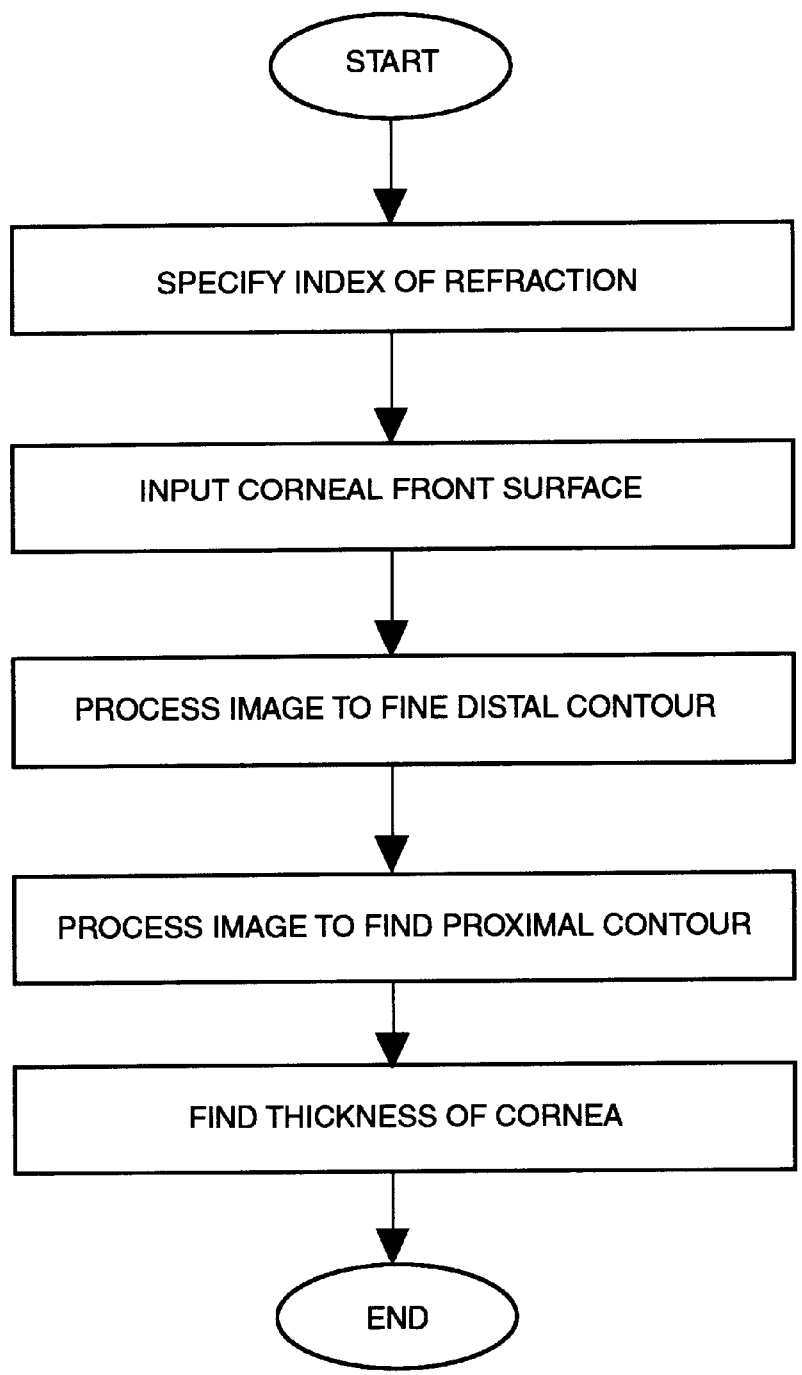
FIG. 5 is a process flow diagram showing the horizontal and vertical cross sections projected onto the eye, in accordance with the principles of the present invention.

FIG. 5 shows a process flow diagram showing the horizontal and vertical cross sections projected onto the eye, in accordance with the principles of the present invention.

In particular, the steps of the exemplary process as shown are:

1. Specify the index of refraction, (about. 1.3771) and input the corneal front surface.

2. Process the image to find the distal contour represented by point B in FIG. 4.

3. Process the image to find the proximal contour represented by point E in FIG. 4.

4. Use ray tracing to find the thickness of the cornea and the points on the corneal back surface.

Corneal Front Surface

Figure 7:
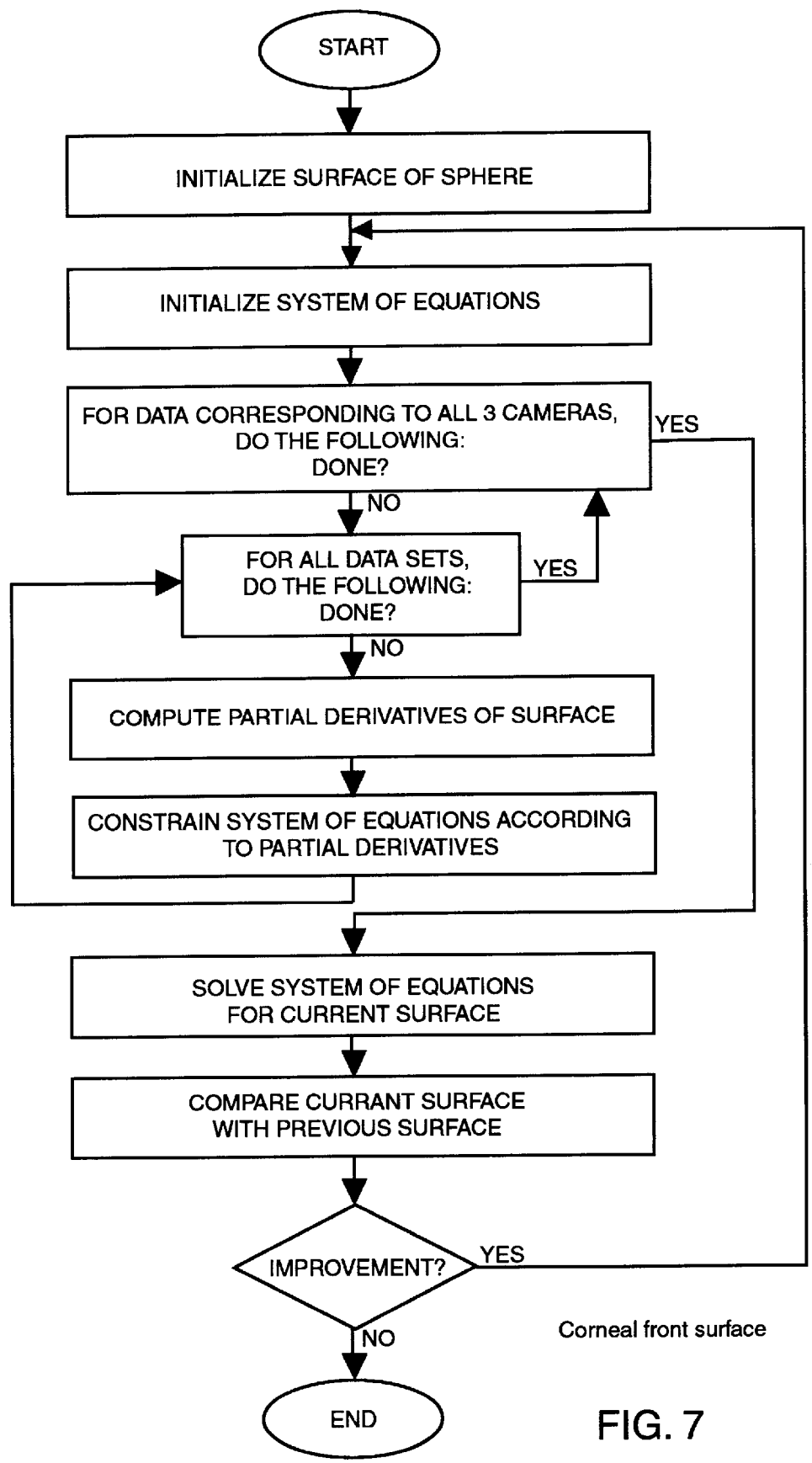
FIG. 7 is a process flow diagram showing an exemplary determination of a corneal front surface, in accordance with the principles of the present invention.

FIG. 6 is a representation of the corneal front surface measurement coverage for three cameras, and FIG. 7 is a process flow diagram showing an exemplary determination of a corneal front surface, in accordance with the principles of the present invention.

In particular, the image processing for the corneal front surface is performed on all three of the left-, front-, and right-view images. For each image we find a set of point correspondences for a given point on the keratometric target and a point on the image. That is, we find the location of the edges in the digitized keratometric images. This edge location data is stored in a M rows by N columns polar array such that M is the number of concentric rings and N is the number of samples (usually 360—one for each degree) in the azimuthal direction. The corresponding keratometric target points are computed during a calibration stage using a known surface and inverse ray tracing. Once the point correspondence has been found for all three images, a single surface is found which incorporates the information from all three images as described in the following:

1. Initialize surface to sphere of radius 7.8.
2. Initialize the system of equations.
3. For data corresponding to all three cameras do the following:
4. For all points for this data set do the following:
5. Use the point correspondence to compute the partial derivatives of the surface.
6. Constrain the system of equations according to the partial derivatives.
7. If more points in this data set, get the next data point and go to step 5.
8. If more data sets, get the next data set and go to step 4.
9. Solve the system of equations for the current surface.
10. Compare the current surface with the previous surface. If no improvement or iteration count exceeded, then exit. Otherwise, go to step 2.

This algorithm can be solved for any surface type. Traditional choices are Zernike polynomials, Taylor polynomials, and splines. Because of its local and controllable nature, the preferred embodiment of the invention uses Bsplines.

Ray Tracing to Compute the Corneal Back Surface and the Thickness

Figure 8:
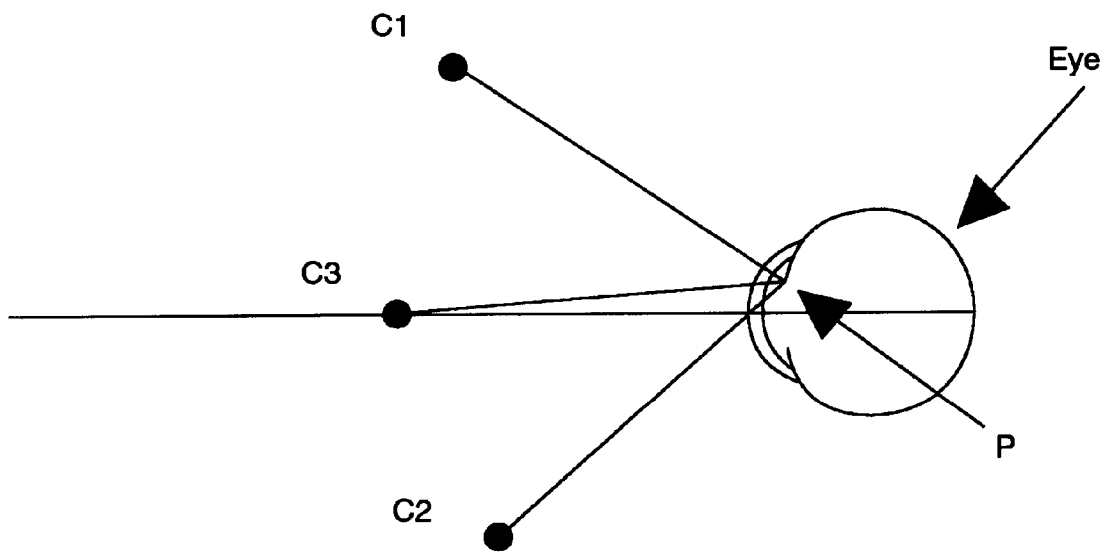
FIG. 8 is a representation of the use of ray tracing to estimate the corneal back surface and corneal thickness.

Prior to performing the reconstruction of the corneal back surface and corneal thickness measurements, the corneal front surface, the pupil contour from all three of the left-, front-, and right-view images, and the projected cross data (corneal front and back surfaces and thickness data for the horizontal and vertical meridians) are known. The fundamental geometry for the use of ray tracing to compute the corneal back surface and corneal thickness is illustrated in FIG. 8. In this figure we see that the rays from the three cameras which correspond to the same point on the pupil contour trace through the cornea at separate points. Knowing the corneal front surface and the index of refraction of the cornea allows rays to be traced through the cornea and intersect the same point at the pupil. The iterative application of this strategy can be employed to estimate the thickness of the cornea and thus estimate the corneal back surface.

Figure 9:
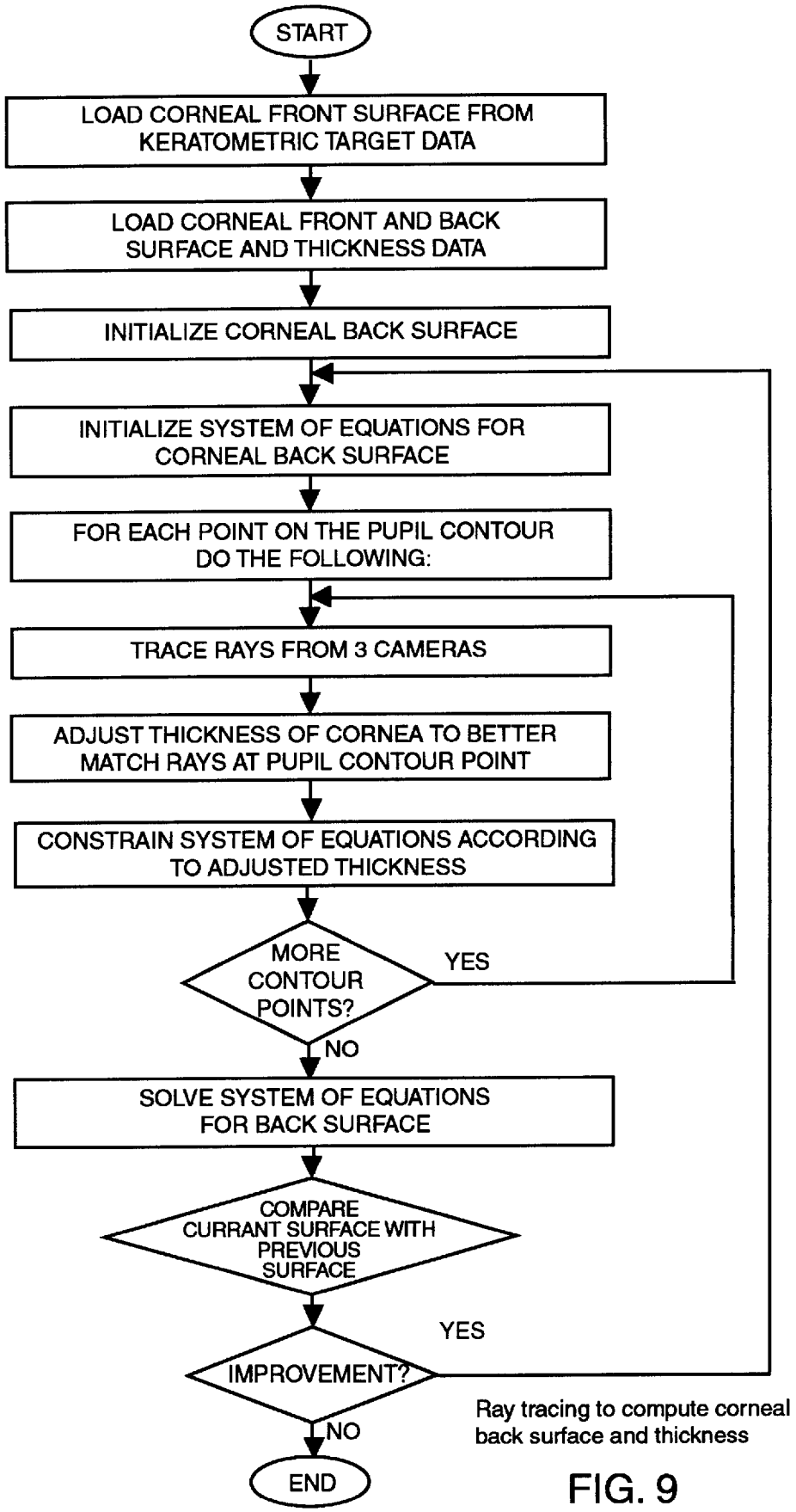
FIG. 9 is a process flow diagram showing an exemplary ray tracing to compute corneal back surface and thickness, in accordance with the principles of the present invention.

FIG. 9 is a process flow diagram showing an exemplary ray tracing to compute corneal back surface and thickness, in accordance with the principles of the present invention.

In particular, as shown in FIG. 9, the exemplary algorithm is as follows:

1. Load the corneal front surface from the keratometric target data.
2. Load the corneal front and back surface and thickness data along the horizontal and vertical meridians from the projected cross data.
3. Initialize the corneal back surface using the horizontal and vertical meridian data from step 2.
4. Initialize the system of equations for the corneal back surface.
5. For each point on the pupil contour do the following:
6. Trace the rays from the three cameras which correspond to the pupil contour.
7. Adjust the thickness of the cornea to better match the rays at the pupil contour point.
8. Constrain the system of equations according to the adjusted thickness found in step 7.
9. If there are more contour points, get the next contour point and go to step 6.
10. Solve the system of equations for the corneal back surface.
11. Compare the current surface with the previous surface. If no improvement or iteration count exceeded, then exit. Otherwise, go to step 4.

Wave Front Aberration

The wave front aberration is computed from the focus mechanism position and both the high- and low-resolution micro-lens array images. The micro-lens array images are processed one at a time. The first to be processed is the low-resolution array image. This is because there are fewer elements to process and it is less sensitive to wave front aberration than the high-resolution array image. The wave front estimated from the low-resolution array image is then used to estimate the location of the high-resolution array image spots. This facilitates a simpler and more robust processing step for the high-resolution array image than is normally possible. The only difference between the processing algorithm for the low-resolution and high-resolution array images is in the search region for the fovial point images. For the low-resolution array image, we search in the neighborhood of the lensletts based on the calibration data (reference point locations) and for the high-resolution array image we use the low-resolution array image results as previously indicated. Because of this similarity, we describe only the low-resolution array processing.

Figure 10:
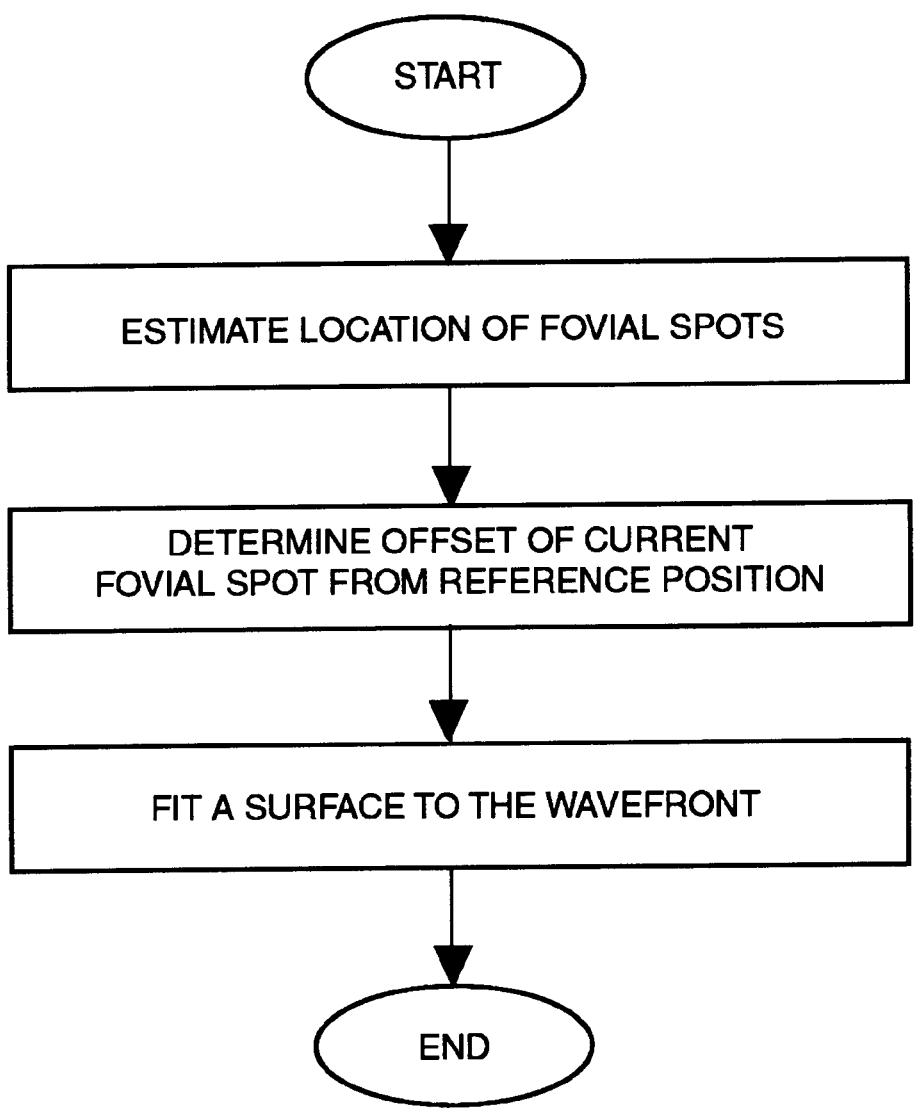
FIG. 10 is a process flow diagram showing an exemplary determination of a wave front aberration, in accordance with the principles of the present invention.
Figure 11A:
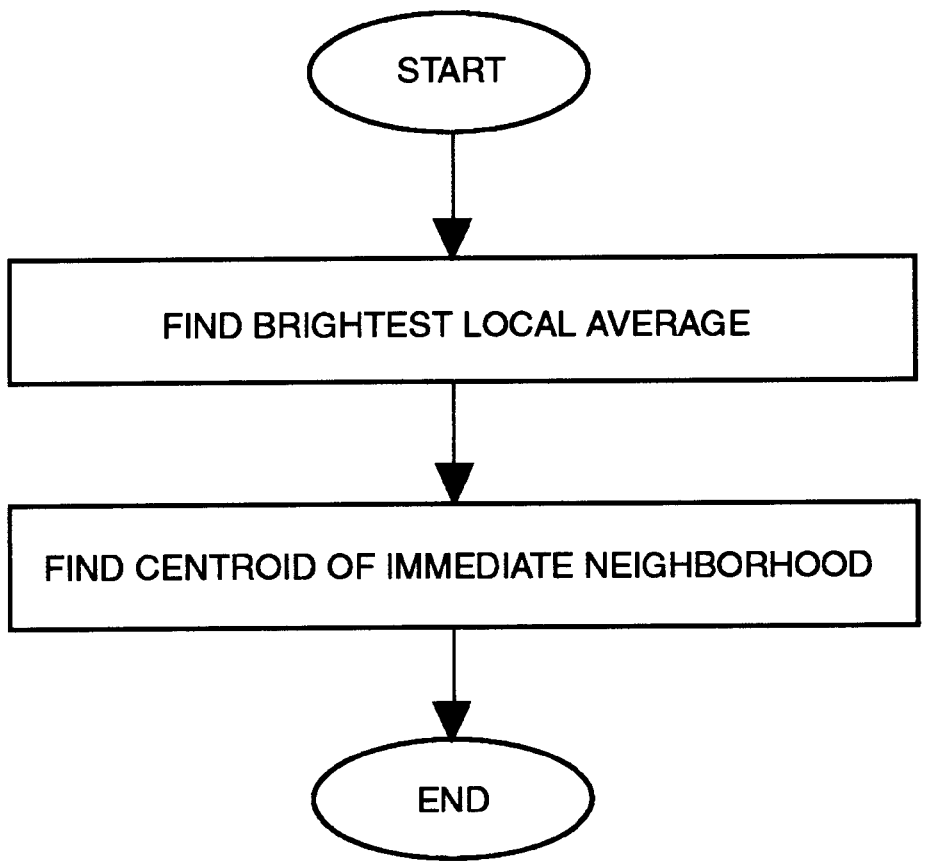
FIG. 11A is a process flow diagram showing an exemplary process of estimating fovial spot locations shown in FIG. 10.
Figure 11B:
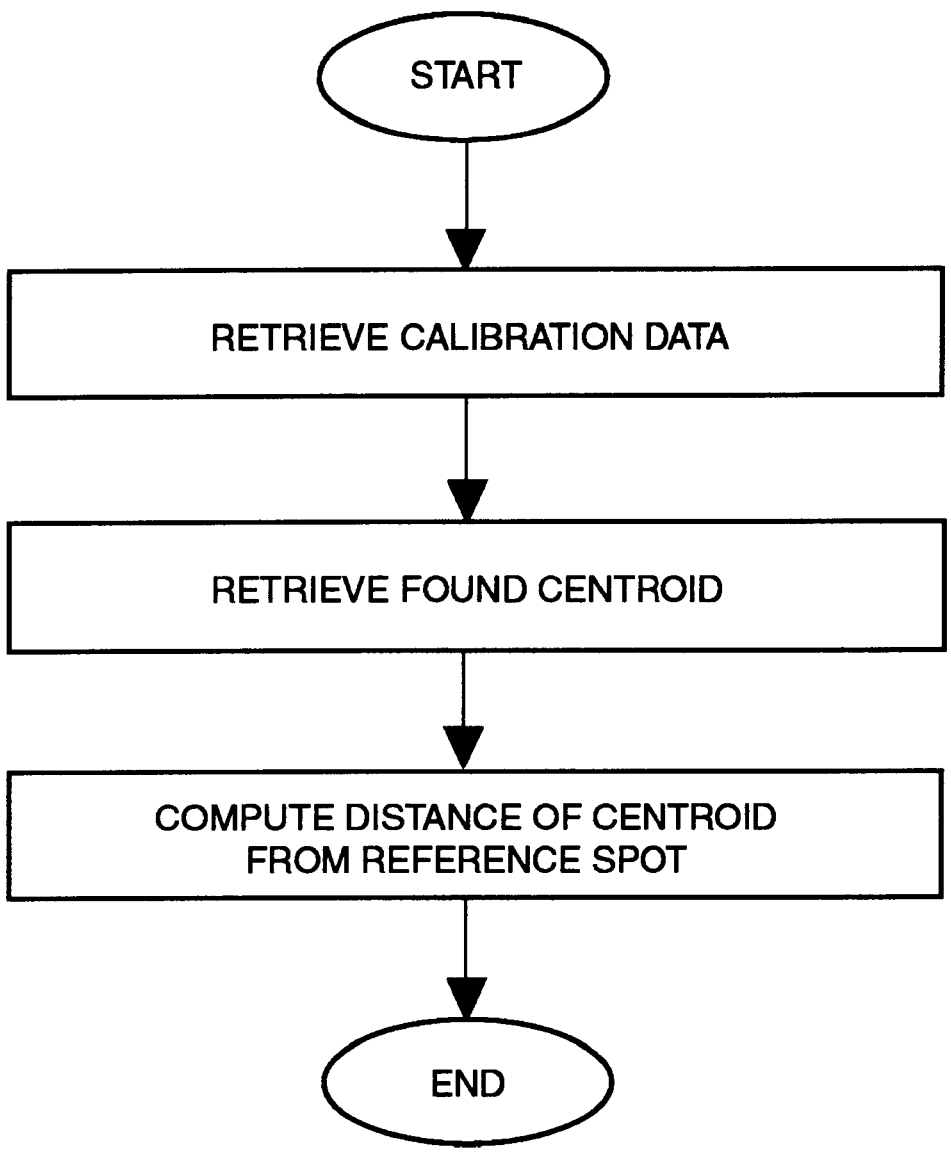
FIG. 11B is a process flow diagram showing an exemplary process of determining offset shown in FIG. 10.
Figure 12:
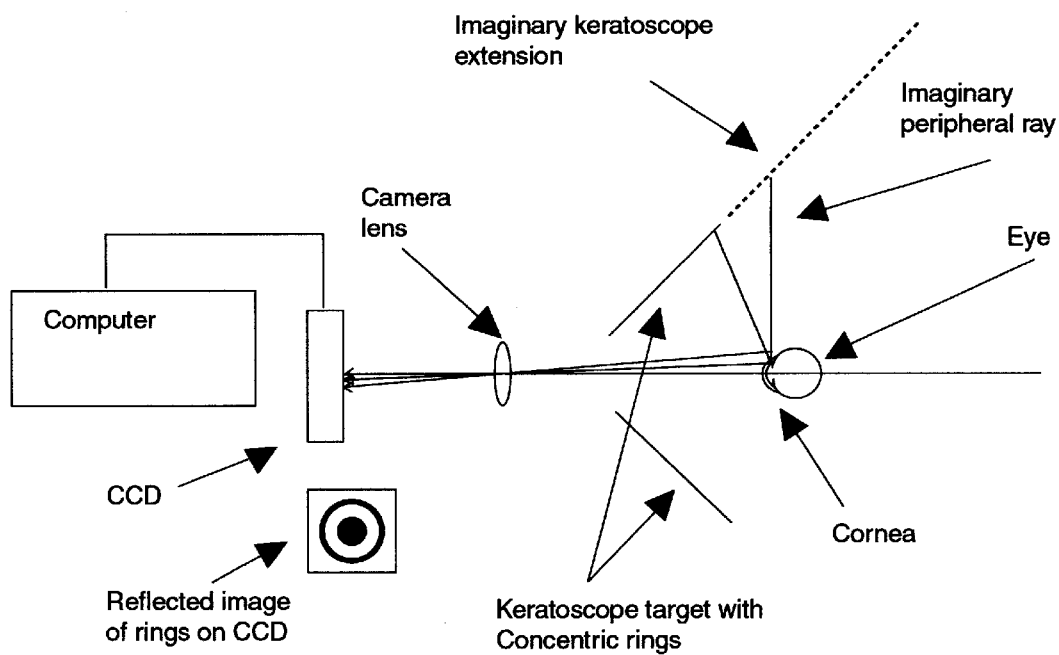
FIG. 12 is a representation of a conventional corneal topography system.
Figure 13:
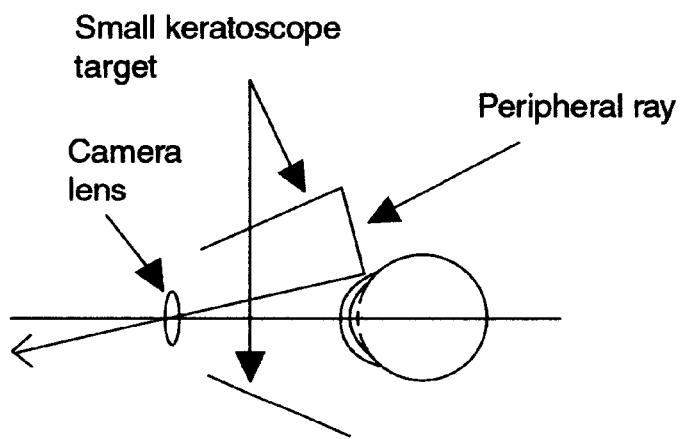
FIG. 13 is a representation of a conventional corneal topography system with a small keratoscope target to try to measure more data in the periphery of the cornea.
Figure 14:
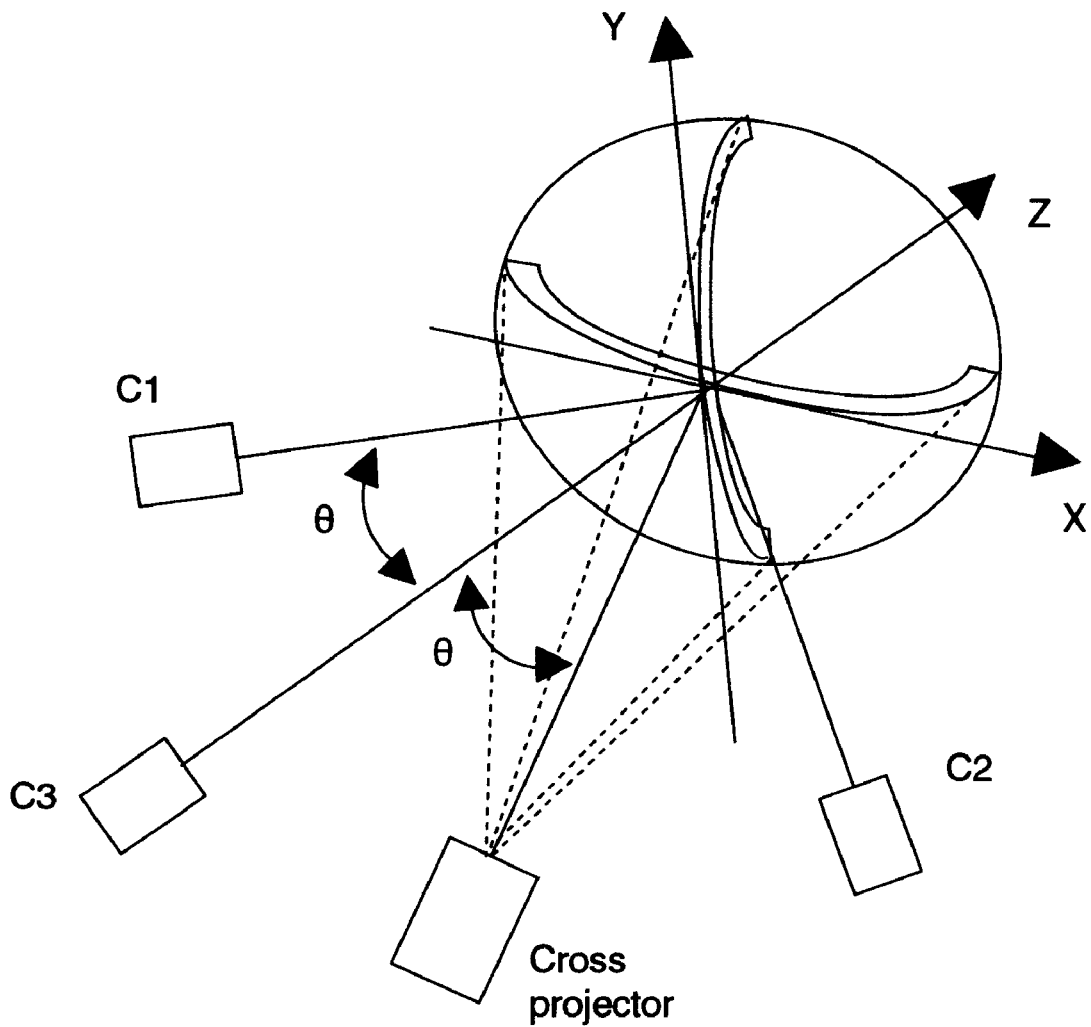
FIG. 14 is a representation of the cross pattern being projected onto the cornea.
Figure 15:
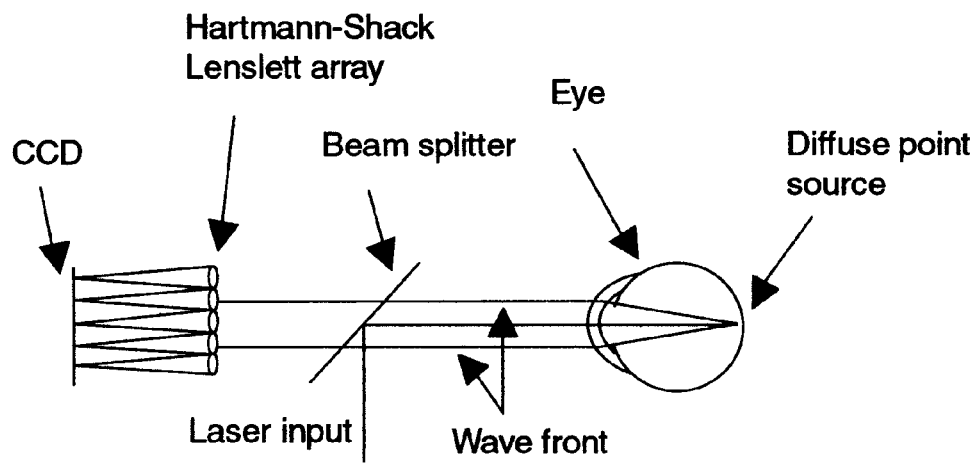
FIG. 15 is a representation of the fundamental operating principals of the Hartmann-Shack wave front aberration measurement.
Figure 16:
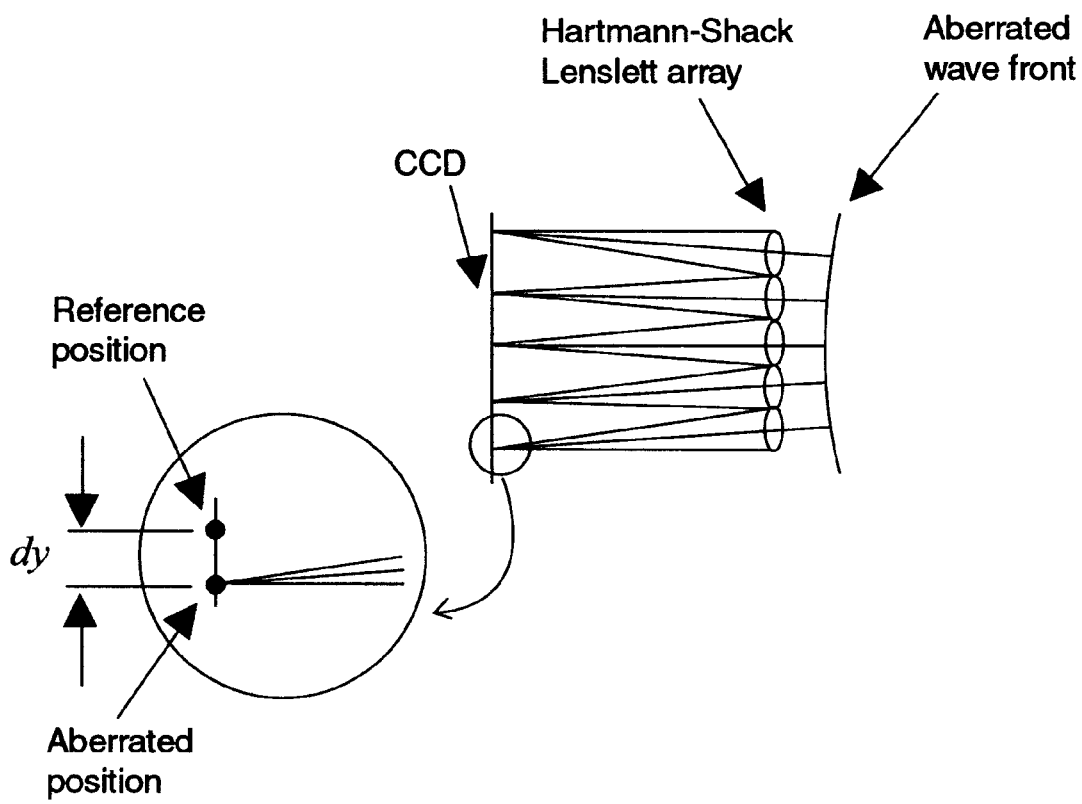
FIG. 16 is a representation of the effect of an aberrated wave front on the Hartmann-Shack lenslett array/CCD image.

FIG. 10 is a process flow diagram showing an exemplary determination of a wave front aberration, in accordance with the principles of the present invention. FIG. 11A is a process flow diagram showing an exemplary process of estimating fovial spot locations shown in FIG. 10, FIG. 11B is a process flow diagram showing an exemplary process of determining offset shown in FIG. 10, FIG. 11C is a process flow diagram showing an exemplary process of fitting a surface to a wave front determined as shown in FIG. 10.

In particular, as shown in FIGS. 10 and 11A to 11C, the algorithm for processing the array image is as follows:

1. Process the image to estimate the location of the fovial spots corresponding to each lenslett.
2. Find the brightest local average inside each search region corresponding to a lenslett.
3. Find the centroid of the immediate neighborhood around the spot found in step 2.
4. Determine the offset of the current fovial spot from the reference position.
5. Using the calibration data and the centroid found above, compute the distance (in millimeters) in the x and y direction of the centroid from the reference spot location.
6. Use the offsets from step 2 to fit a surface to the wave front.
7. Initialize a system of equations.
8. For each fovial spot found add two equations to the systems of equations. One for a constraint from the partial derivative with respect to x and one for a constraint based on the partial derivative with respect to y.
9. Solve the system of equations.

This algorithm can be solved for any surface type. Traditional choices are Zernike polynomials, Taylor polynomials, and splines. Because of its common use in optical wave front analysis, the preferred embodiment of the invention uses Zernike polynomials.

While the invention has been described with reference to the exemplary embodiments thereof, those skilled in the art will be able to make various modifications to the described embodiments of the invention without departing from the true spirit and scope of the invention.

What is claimed is:

1. A method for determining wave front aberration, comprising:

estimating a location of a fovial spot;

finding a brightest local average in said fovial spot;

finding a centroid of an immediate neighborhood around said fovial spot;

determining an offset of said fovial spot from a reference position;

computing a distance of said centroid from said reference position; and fitting a surface to a wave front using said determined offset.

2. The method for determining wave front aberration according to claim 1, further comprising:

initializing a system of equations; and adding at least two equations to said system of equations corresponding to said fovial spot.

3. The method for determining wave front aberration according to claim 2, wherein:

one of said at least two equations corresponds to a constraint from a partial derivative with respect to x; and the other of said at least two equations corresponds to a constraint based on a partial derivative with respect to y.

4. The method for determining wave front aberration according to claim 3, further comprising:

solving said system of equations.

* * * * *